United States Patent [19]

Dasek et al.

[11] 3,933,591

[45] Jan. 20, 1976

[54] PROCESS FOR PREPARING INTRACELLULAR SUBSTANCES OF MICROBIAL ORIGIN

[75] Inventors: Jaroslav Dasek, Yverdon; Knut Rude Traelnes, Renens, both of Switzerland

[73] Assignee: Societe d'Assistance Technique pour Produits Nestle S.A., Lausanne, Switzerland

[22] Filed: Apr. 27, 1973

[21] Appl. No.: 355,014

[30] Foreign Application Priority Data
May 3, 1972 Switzerland................ 6589/72

[52] U.S. Cl.................. 195/96; 195/108; 195/104
[51] Int. Cl.² .......................................... C12B 1/00
[58] Field of Search ......... 195/28 N, 108, 104, 112, 195/65, 96

[56] References Cited
UNITED STATES PATENTS

| 3,243,354 | 3/1966 | Nakao et al. | 195/28 N |
|---|---|---|---|
| 3,275,610 | 9/1966 | Coty | 195/104 |
| 3,359,177 | 12/1967 | Nara et al. | 195/28 N |
| 3,616,211 | 10/1971 | Pietsch | 195/28 N |
| 3,719,754 | 3/1973 | Day et al. | 195/28 N |

*Primary Examiner*—Alvin E. Tanenholtz
*Attorney, Agent, or Firm*—Watson Leavenworth Kelton & Taggart

[57] ABSTRACT

Intracellular substances of microbial origin are prepared by culturing a microorganism in a suitable nutrient medium therefor in the presence of at least one antibiotic in sufficient amount to weaken the walls of the microorganism cells but insufficient to arrest growth of the microorganism and induce discharge of the intracellular substances into the culture medium, thereafter rupturing the walls of at least a part of the microorganism cells and recovering the intracellular substances released by rupture of the cell walls.

8 Claims, No Drawings

PROCESS FOR PREPARING INTRACELLULAR SUBSTANCES OF MICROBIAL ORIGIN

The present invention is concerned with the production of intracellular substances of microbial origin, such as enzymes, nucleic acids or pigments.

The industrial preparation of these intracellular substances, particularly of proteins of microbial origin, generally involves their extraction from the cells of the microorganism. This extraction implies that the substances contained within the microbial cells overcome the barrier which is the cell wall, and it is frequently necessary, in order to obtain a satisfactory extraction yield, to rupture the cell wall.

This may be effected by chemical or enzymatic hydrolysis of the substances making up the cell wall. However, chemical hydrolysis, which generally has to be carried out under more or less extreme conditions, frequently causes deterioration of the nutritive value of the proteins sought to be liberated. Furthermore such chemical hydrolysis implies addition of hydrolytic agents which subsequently need to be removed from the product. On the other hand, enzymatic hydrolysis is generally too expensive for application in an industrial process.

Another known process comprises addition of an antibiotic to the culture medium at a high concentration to induce discharge of intracellular substances, particularly proteins, directly into the fermentation broth. However, this process, which involves the use of large amounts of antibiotic, is relatively uninteresting from the economic standpoint and has the disadvantage of seriously disturbing the growth kinetics of the microorganism. Moreover, this process implies separation of the discharged substances from the culture medium, involving handling of very substantial quantities of starting material as compared with the quantity of the substances extracted.

A further known process consists in causing rupture of the cell walls by mechanical forces using disintegration devices such as special grinders, homogenisers or ultrasonic apparatus. However, the mechanical resistance of cell walls is such that rupture of the walls occurs only in a relatively small proportion of the cells. The result is frequently an extraction yield insufficient for industrial operations.

The present invention provides a particularly simple process for preparing intracellular substances of microbial origin, which comprises culturing a microorganism in a suitable nutrient medium therefor in the presence of at least one antibiotic in sufficient quantity to weaken the walls of the microorganism cells, but insufficient to arrest growth of the microorganism and induce discharge of the intracellular substances into the culture medium, thereafter rupturing the walls of at least a part of the microorganism cells and recovering the intracellular substances released by rupture of the cell walls.

The expression "suitable nutrient medium" denotes, in the following specification, a medium containing the substances necessary for life and multiplication of the microorganism cells. These substances include, e.g., carbon and nitrogen sources, for example carbohydrates and/or hydrocarbons, nitrogenous substances, as well as mineral salts. This nutrient medium may also contain growth factors such as vitamins, as well as oxygen if the microorganism lives and reproduces under aerobic conditions.

Likewise, the expression "to weaken the walls of the microorganism cells" means, in the following specification, that defects not present in the walls of cells cultured in a medium not containing an antibiotic are produced in the structure and/or the geometry of the walls, these defects causing a decrease of the mechanical resistance of the cell without however inducing rupture or opening of the cell wall.

The resulting microbial cells are then subjected to a mechanical treatment producing rupture of the cell walls and liberation of the substances contained in the cells. Although not essential, it is preferable to separate the biomass from the culture medium before effecting the mechanical disintegration treatment. This operation, which may be effected in any convenient manner such as decanting, filtration or centrifugation, leads to a considerable reduction in the amounts of material to be treated in the fragmentation step.

The treated cell mass, that is after mechanical rupture of the cell walls, may be used for the preparation of a range of substances extending from adhesives and resins to protein foodstuffs. For example the fragments of ruptured cell walls may be separated from the protein, if necessary after solubilisation of the latter, by centrifugation, and the protein precipitated, for example by acidification. According to a variant, the protein may be subjected to enzymatic hydrolysis to provide peptides which may then be recovered by an appropriate technique (precipitation, separation, washing, etc.). The fragmented cell mass may also be utilised as such, for example in the production of a textured product by extrusion or spinning, with suitable adjustment of the pH to solubilise the protein.

The process according to the invention is particularly effective on bacteria, and it has been found for example that a fragmented bacterial biomass obtained by this process may without difficulty be transformed into protein fibres by spinning.

The appropriate antibiotic concentration in the culture medium, which produces the desired effect, that is weakening of the cell walls of the microorganism, is dependent both on the type of microorganism and of antibiotic. Application of the process according to the invention thus includes determination of the suitable concentration range corresponding to the microorganism-antibiotic system used. The upper limit of this range may be determined, for the system considered, by measuring the antibiotic concentration in the medium beyond which growth of the microorganism is arrested, which generally occurs a certain time after the antibiotic has been added to the culture medium. Thus for example for the bacterium Sarcina lutea the antibiotic concentrations beyond which growth is stopped are 0.05 International Units for penicillin G, 100 $\mu$g/ml for D-cycloserine and 30 $\mu$g/ml for bacitracin. The lower limit of the concentration range is generally around 5% of the value of the upper limit of this range, which means that at concentrations below this limit the weakening of the cell walls becomes insignificant and has practically no influence on the fragmentation yield of the cells in the subsequent rupture operation. The antibiotic concentration of the culture medium for a given system may be selected between the two limiting values having regard to particular application criteria of the process. For example, an antibiotic concentration may be selected in the upper part of the appropriate range, which leads to a slight decrease in the growth rate of the microorganism, which is combined with a substantial increase in the number of cells ruptured for a given disintegration energy input (for example for a particular operating pressure of a homogeniser). If on the other hand it is undesirable to modify the growth kinetics of the microorganism to any substantial extent, lower antibiotic concentrations may be used, which implies that more energy is required for fragmentation than in the preceding case, insofar as a fragmentation yield of about the same order is desired.

According to one embodiment of the process according to the invention, a microorganism is cultured in a suitable nutrient medium and the resulting culture is inoculated into a nutrient medium in a fermenter. Growth of the microorganism is sustained by providing proper oxygenation of the medium and maintenance of an adequate temperature, generally of the order of 20° to 50°C, and an appropriate pH, between 3.0 and 8.0.

An antibiotic is then added to the culture medium, preferably during the exponential growth phase of the microorganism, in an amount such that growth is not arrested and the proteins contained in the cells are not discharged into the culture medium. In many cases, this addition has only a slight effect on the multiplication kinetics of the microorganism, and the resulting decrease in growth rate is below 20%. Culture of the microorganism is continued under these conditions for several hours and the biomass is then recovered from the culture medium, for example by centrifuging, decanting or filtration, washed and suspended in water. This suspension is then subjected to a mechanical treatment, for example with ultrasonic waves or suitable homogeniser or mill, which causes rupture of the cell walls.

In a variant of this embodiment, a mixture of several antibiotics may be added to the culture medium in amounts such that growth of the cells is not stopped and the cell proteins are not discharged into the culture medium.

According to another embodiment of the process according to the invention culture of the microorganism is effected in continuous manner in a fermenter, by continuously supplying to the fermenter a suitable nutrient medium containing one or more antibiotics. The contents of this medium and the rate of supply are regulated so that growth of the microorganism is not stopped and that the cell proteins are not discharged into the culture medium. The biomass, recovered by centrifugation of the effluent drawn from the fermenter is suspended in water, preferably after being washed, and subjected to mechanical treatment in conventional manner.

The following examples describe several applications of the process according to the invention by way of illustration.

In these examples the proportions and percentages are expressed on a weight basis.

EXAMPLE 1

A *Sarcina lutea* bacterium is cultured in 1.5 liters of a sterilised aqueous nutrient medium the pH of which was adjusted, before sterilisation, to 6.5. The medium has the following composition:

| | |
|---|---|
| $NH_4Cl$ | 0.1 % |
| $MgSO_4.7H_2O$ | 0.05 % |
| $K_2HPO_4$ | 0.1 % |

-continued

| | |
|---|---|
| $FeSO_4.7H_2O$ | 0.001 % |
| $CaCl_2$ | 0.001 % |
| Peptone | 1.0 % |
| Yeast extract | 0.5 % |
| Sucrose | 0.5 % |
| Tap water | balance to 100 % |

Culture is continued for 24 hours at 25°C under aerobic conditions in a flask shaken by rotation. The resulting culture is then inoculated into 9 liters of aqueous culture medium in a 14-liter fermenter. This culture medium has the same composition as the medium described previously, except that the yeast extract and sucrose levels are increased to 1% and 2% respectively.

Growth of the bacterium is sustained in the fermenter, at a temperature of 25°C, with agitation of the culture medium with a stirrer rotating at 250 r.p.m., aeration being provided by supplying 7 liters of air per minute at atmospheric pressure.

During the exponential growth phase, penicillin G is added to the medium to obtain a penicillin concentration in the medium of 0.04 International Units per ml of culture medium.

Culture of the bacterium is continued for 9 hours and the bacterial cells are separated from the culture medium by centrifugation. The recovered cells are washed and suspended in water at a level of 80 g dry matter per liter of water. This aqueous suspension is then treated mechanically in a RIBI disintegrator (manufactured by Ivan Sorvall Inc., Norwalk, Conn.) at a pressure between 700 and 1000 atmospheres.

The amount of broken cells, determined by estimation of liberated nitrogen, corresponds to 20% of the total number of cells.

Identical mechanical treatment of *Sarcina lutea* cells cultured under the same conditions, but without antibiotic, leads to rupture of only 4% of the cells.

On the other hand addition to the culture medium of penicillin G at a level of 0.04 International Units per ml of culture broth increases the growth time of the organism by only 10%, which shows that this addition has only a slight influence on the reproduction kinetics of the microorganism.

EXAMPLE 2

A *Bacillus megatherium* bacterium is cultured in 0.05 liters of an aqueous nutrient medium the pH of which is adjusted to 6.5 before sterilisation. The composition of the medium is:

| | |
|---|---|
| $(NH_4)_2HPO_4$ | 1 % |
| $K_2HPO_4$ | 0.5 % |
| $Na_2SO_4$ | 0.5 % |
| $MgSO_4.7H_2O$ | 0.4 % |
| $FeSO_4.7H_2O$ | 0.002 % |
| NaCl | 0.002 % |
| Yeast extract | 0.025 % |
| Corn steep liquor | 0.025 % |
| Sucrose | 2.0 % |
| Tap water | balance to 100 % |

Incubation is continued for 24 hours at 30°C, under aerobic conditions, with shaking. 5% of the resulting broth is then inoculated into 9 liters of an aqueous nutrient medium in a 14-liter fermenter and having the same chemical composition as the incubation medium. Culture of the bacterium is sustained at a temperature of 30°C, with stirring at 250 r.p.m., with air supplied at atmospheric pressure at a rate of 7 liters per minute.

During the exponential growth phase 4 µg/ml of bacitracin are added to the culture medium.

After 9 hours of culture under these conditions, the bacterial cells are separated from the culture medium by centrifugation. The recovered cells, washed and suspended in water, are subjected to the mechanical treatment described in example 1.

The amount of ruptured cells, determined as described in example 1, corresponds to 61% of the total number of cells. Identical mechanical treatment of *Bacillus megatherium* cells cultured under the same conditions but without antibiotic causes rupture of only 26% of the cells.

EXAMPLE 3

A *Micrococcus cerificans* bacterium is cultured in an aqueous nutrient medium having the following composition:

| | |
|---|---|
| $(NH_4)_2HPO_4$ | 1 % |
| $K_2HPO_4$ | 0.5 % |
| $Na_2SO_4$ | 0.5 % |
| $MgSO_4.7H_2O$ | 0.4 % |
| $FeSO_4.7H_2O$ | 0.002 % |
| NaCl | 0.002 % |
| Yeast extract | 0.025 % |
| Corn steep liquor | 0.025 % |
| Mixture of $C_{12}-C_{20}$ linear paraffins | 2.0 % |
| Tap water | balance to 100 % |

Culture is carried out in a fermenter at 30°C under aerobic conditions and cycloserine is added to the culture medium during the exponential growth phase at a level of 100 µg of cycloserine per ml of culture broth.

After 9 hours' culture under these conditions, the cells are recovered and treated mechanically as described in example 1. The amounts of cells broken, respectively for a culture effected in the presence of antibiotic and a culture effected without antibiotic, are 75% and 57%.

EXAMPLE 4

A *Bacillus megatherium* bacterium is cultured in continuous manner, by charging into a fermenter a broth obtained by culture of the bacterium in the medium described in example 2 and under the same conditions (without addition of antibiotic). The fermenter is supplied continuously with aqueous nutrient medium identical with the preceding but to which penicillin G has been added at a level of 1.5 International Units per ml.

The biomasss separated by centrifugation from the effluent drawn from the fermenter is washed, suspended in water and treated in a Manton Gaulin homogeniser at a pressure of 700 atmospheres.

This mechanical treatment causes rupture of 65% of the cells cultured in this manner whereas the same treatment applied to cells of the same microorganism cultured under the same conditions but in the absence of antibiotic ruptures only 20% of these cells.

EXAMPLE 5

A *Sarcina lutea* bacterium is cultured in continous manner in the culture medium described in example 1. The culture medium, fed continuously into the fermenter, contains 0.04 International Units of penicillin G per ml.

The cells recovered from the effluent drawn from the reactor, after washing and suspension in water, are treated as described in example 4. 25% of these cells are ruptured whereas the degree of rupture of cells treated under the same conditions, but cultured in the absence of antibiotic, is only 5%.

EXAMPLE 6

*Lactobacillus helveticus* bacterium, ATCC No. 15807, is cultured aerobically in a nutrient medium consisting of a solution in demineralised water of 6% by weight of whey solids and 0.1% by weight of corn steep liquor, this solution having been sterilised by heating at 120°C for 30 minutes. Culture is effected in a 14-liter fermenter at a temperature of 42°C, mixing being provided by slow rotation of the stirrer at 15 r.p.m. and the pH of the medium being maintained at 5.5 by addition of dilute aqueous potassium hydroxide solution. 5 hours after inoculation of the bacterium into the culture medium a sterile solution of penicillin G is added to provide a concentration in the medium of 0.03 International Units per ml. Culture is continued for 15 hours under these conditions and 9 liters of the resulting culture broth are then withdrawn. The cells are then separated from the culture medium by centrifugation, are washed and suspended in water. This aqueous suspension is treated mechanically in a Manton Gaulin homogeniser at a pressure of 700 atmospheres in one pass. This mechanical treatment causes rupture of 90% of the cells, whereas the same treatment applied to 9 liters of a suspension of the same microorganism obtained by culture under the same conditions in the same medium, but without addition of antibiotic to the culture medium, ruptures only 55% of the cells.

EXAMPLE 7

A *Sarcina lutea* bacterium is cultured in continuous manner in an aqueous nutrient medium having the following composition:

| | |
|---|---|
| $NH_4Cl$ | 0.1 % |
| $MgSO_4.7H_2O$ | 0.05 % |
| $K_2HPO_4$ | 0.1 % |
| $FeSO_4.7H_2O$ | 0.001 % |
| $CaCl_2$ | 0.001 % |
| Peptone | 1.0 % |
| Yeast extract | 0.5 % |
| Sucrose | 1.5 % |
| Tap water | balance to 100 % |

This nutrient medium, fed continuously into the fermenter, contains 004 International Units of penicillin G per ml. Culture is effected aerobically at a temperature of 27°C with stirring at 400 r.p.m.

The cells, recovered from the effluent withdrawn from the fermenter, are washed, suspended in water and treated in a Dyno-Mill homogeniser at a rate of 5 liters/hour, the apparatus being equipped with glass beads 0.2 mm in diameter. 85% of these cells are ruptured, whereas the same mechanical treatment applied to a suspension of cells cultured under the same conditions, but without antibiotic, ruptures only 65% of the cells.

We claim:

1. In a process for preparing intracellular substances of microbial origin, which comprises culturing a microorganism in a suitable nutrient medium therefor, mechanically rupturing the walls of at least a part of the microorganism cells and recovering the intracellular substances released by such rupture, the improvement which comprises adding to said medium at least one antibiotic in an amount sufficient to weaken the walls of the microorganism cells but insufficient to arrest growth of the microorganism cells or to induce discharge of intracellular substances into said medium, whereby cells exhibiting such weakened cell walls are cultured.

2. A process according to claim 1, in which the microorganism cells are separated from the nutrient medium before the walls of the cells are ruptured.

3. A process according to claim 1, in which the antibiotic is added to the culture medium during the exponential growth phase of the microorganism.

4. A process according to claim 1, in which the antibiotic is a penicillin, bacitracin or cycloserine.

5. A process according to claim 2, in which the antibiotic is added to the culture medium during the exponential growth phase of the microorganism.

6. A process according to claim 2, in which the antibiotic is a penicillin, bacitracin or cycloserine.

7. A process according to claim 5, in which the antibiotic is a penicillin, bacitracin or cycloserine.

8. A process according to claim 1 in which the microorganism comprises bacteria.

* * * * *